US009147343B2

(12) United States Patent
Johnson et al.

(10) Patent No.: US 9,147,343 B2
(45) Date of Patent: Sep. 29, 2015

(54) EXERCISE USAGE MONITORING SYSTEM

(71) Applicant: ECOFIT Networks Inc., Victoria (CA)

(72) Inventors: David Johnson, Victoria (CA); Philip Rankine, Victoria (CA); Peter McGuire, Victoria (CA)

(73) Assignee: ECOFIT Networks Inc., Victoria (CA)

( * ) Notice: Subject to any disclaimer, the term of this patent is extended or adjusted under 35 U.S.C. 154(b) by 145 days.

(21) Appl. No.: 13/687,653

(22) Filed: Nov. 28, 2012

(65) Prior Publication Data

US 2013/0135115 A1 May 30, 2013

Related U.S. Application Data

(60) Provisional application No. 61/565,236, filed on Nov. 30, 2011.

(51) Int. Cl.

*G08B 23/00* (2006.01)
*G08C 19/00* (2006.01)
*H04Q 9/00* (2006.01)

(52) U.S. Cl.

CPC .................. *G08C 19/00* (2013.01); *H04Q 9/00* (2013.01); *H04Q 2209/47* (2013.01); *H04Q 2209/75* (2013.01); *H04Q 2209/86* (2013.01)

(58) Field of Classification Search

CPC ................................... H04Q 1/00; G01D 1/00
USPC .............. 340/870.02, 870.07, 3.1, 4.32, 5.61; 482/8, 9
See application file for complete search history.

(56) References Cited

U.S. PATENT DOCUMENTS 6,991,586 B2 1/2006 Lapcevic
8,088,044 B2 * 1/2012 Tchao et al. ...................... 482/8
8,118,709 B2 2/2012 McKirdy et al.
8,915,823 B2 12/2014 McKirdy et al.
2003/0005137 A1 * 1/2003 Yu ................................ 709/230
2011/0090092 A1 * 4/2011 Birrell et al. ............. 340/870.07
2012/0116554 A1 5/2012 McKirdy et al.

OTHER PUBLICATIONS

"Fit for Green: The Social Green—Workout," product pamphlet, www.fitforgreen.com, 2 pages.
Pat Brennan, "Gym Generates Electricity—and Competition," article, The Orange County Register, http://www.ocregister.com/articles/-338021--.html, Jan. 30, 2012.

* cited by examiner

*Primary Examiner* — Vernal Brown
(74) *Attorney, Agent, or Firm* — Lempia Summerfield Katz LLC

(57) ABSTRACT

The disclosed embodiments relate to real time monitoring of usage of multiple pieces of exercise equipment and providing exercise based metric data based thereon to devices for aggregation, display or other processing thereof. In particular, the disclosed embodiments facilitate collection of exercise based metric data from various pieces of exercise equipment, such as stationary bikes, treadmills, and the like, in real time, i.e. as the equipment is utilized by an exercising user, combine the collected data in a form suitable for use by various interested devices and broadcast or otherwise disseminate the combined data to the various devices wherein the various devices may access the broadcasted combined data to access the usage metric data from any one or more of the pieces of exercise equipment from which it was collected for subsequent aggregation, display and/or further processing.

29 Claims, 9 Drawing Sheets

EXERCISE USAGE MONITORING SYSTEM

REFERENCE TO RELATED APPLICATIONS

This application claims the benefit of the filing date under 35 U.S.C. §119(e) of U.S. Provisional Application Ser. No. 61/565,236 filed Nov. 30, 2011, which is hereby incorporated by reference.

BACKGROUND

Monitoring systems for exercise equipment, such as stationary bicycles, treadmills, elliptical machines and the like, are known to measure, track and display the progress of a users exercise routine. Monitoring may be performed, for example, by a user at a machine via a local display which may be either embedded in the exercise equipment or provided nearby, in order for the user to track their progress during a workout with exercise metrics, e.g. calories burned, watts generated, floors climbed, distance traversed, etc., linked to their workout. Additionally, users may be given the ability to store their metrics from a workout session. This is advantageous for the user as it provides the ability to track progress over time. If a user, for example, monitors and stores the metric of "average speed" or "distance" on a exercise bike, they may gain valuable feedback on their progress over many sessions. Likewise a fitness/health club facility may wish to track individual or groups of users in order to collect usage and training information, which can be used by the facility to, for example, ascertain popular machines and help encourage and increase the results of their uses.

To facilitate monitoring the status or progress of users of exercise equipment and their metrics, the exercise equipment may provide access to the usage data via a communications protocol, such as C-SAFE or ANT+, which are known in the art. The use of these protocols allow a monitoring system connected to the exercise equipment to access usage data, often for re-presentation to a user via a display device.

Monitoring systems, which include exercise systems that track and store both equipment use and user workout data in a data storage network, are available. One such system is described in U.S. Pat. No. 6,991,586 which discloses a system which captures data from multiple sources, such as exercise equipment, and stores it on a computer server for permanent storage or interactive analysis of the data combined with entertainment system data. It allows a user to integrate data from a personal monitoring device, such as a heart-rate device, as well as data from exercise equipment and display the data for a user. Unfortunately, if a user wishes to monitor the status of their exercise session, they are limited to doing so via the provided viewing screen. As a result users are limited from customization and further interaction with the data as they exercise which may enhance their overall experiences with the exercise sessions. Accordingly there is a need to provide an exercise usage monitoring system that improves the convenience and enhances a users workout experience, as well as optimizes the equipment owner's resources and experiences.

DETAILED DESCRIPTION

The disclosed embodiments relate to substantially real time monitoring of usage of multiple pieces of exercise equipment and providing exercise based metric data based thereon to devices for aggregation, display and/or other processing thereof, such as for computation of statistics, fostering of competition among users, equipment maintenance, etc. In particular, the disclosed embodiments facilitate collection of exercise based metric data from various pieces of exercise equipment, such as stationary bikes, treadmills, and the like, in real time, i.e. as the equipment is utilized by an exercising user, combine the collected data in a form suitable for use by various interested devices and broadcast or otherwise disseminate the combined data to the various devices in a readily accessible format wherein the various devices may access the broadcasted combined data to access the usage metric data of interest from any one or more of the pieces of exercise equipment from which it was collected for subsequent aggregation, display and/or further processing.

Figure 1:
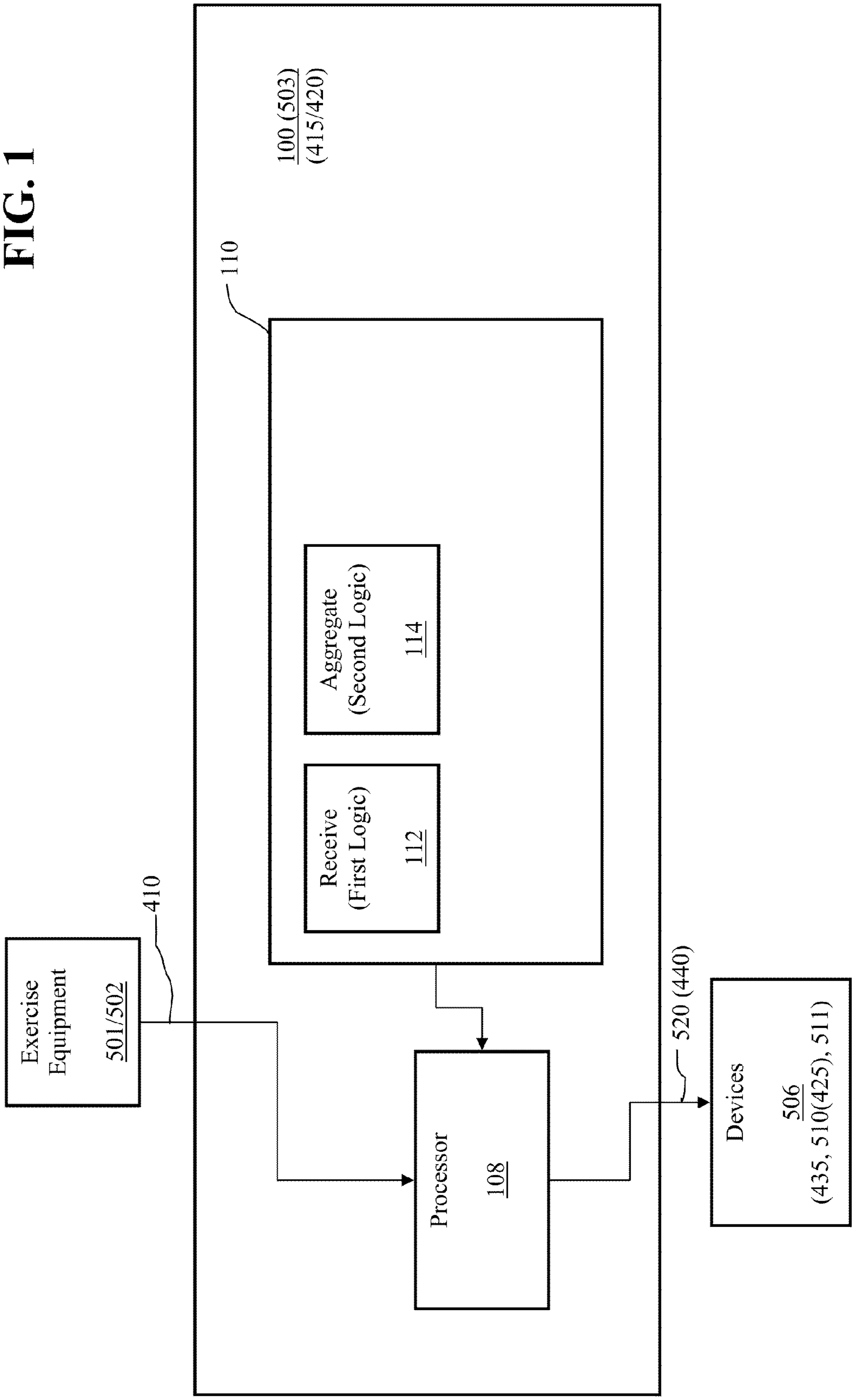
FIG. 1 is a block diagram of an exemplary implementation of a system for monitoring and broadcasting exercise based metrics described herein.

In one embodiment, a system 100 is provided for monitoring usage of a plurality of pieces of exercise equipment 501. In one embodiment, the system 100 is implemented as part of an ECOFIT installation, described in more detail below, manufactured by ECOFIT Networks, located in Victoria, British Columbia, Canada. In particular, FIG. 1 shows a system 100 which generally may include a processor 108 and a non-transitory memory 110 coupled therewith and which may be implemented by one or more of the processor 302 and memory 304 as described below with respect to FIG. 3. In particular, the system 100 may be implemented, at least in part, in an application specific device, desktop computer, portable computer, mobile device, such as a cellular telephone, smart phone, mobile navigation device or tablet computing device. Further, one or more parts of the system 100 may be implemented in a server, e.g. remote from the desktop/portable computer or mobile device, coupled therewith via a network, such as a wired or wireless network, or combination thereof, e.g. the network 320 described below with respect to FIG. 3. In one embodiment, the system 100 implements the base station 415 and aggregator 420, which may be implemented separately or in combination 503, described in more detail below. For example, the base station 415 may be implemented as a standalone application specific device enclosed in a housing and including the necessary hardware, e.g. radios, processors, memory, etc. and software, and coupled with the aggregator 420, such as via a wired or wireless connection, which may be implemented as a separate standalone device enclosed in a housing, or in a computer or other device as described. Alternatively, the functionality of both the base station 415 and aggregator 420 may be combined in a singular device as described. It will be appreciated that the physical arrangement of described functionality is dependent upon the implementation and that all physical arrangements which implemented the described functionality, now available or later developed are contemplated herein.

Herein, the phrase "coupled with" is defined to mean directly connected to or indirectly connected through one or more intermediate components. Such intermediate components may include both hardware and software based components. Further, to clarify the use in the pending claims and to hereby provide notice to the public, the phrases "at least one of <A>, <B>, . . . and <N>" or "at least one of <A>, <B>, . . . <N>, or combinations thereof" are defined by the Applicant in the broadest sense, superseding any other implied definitions herebefore or hereinafter unless expressly asserted by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

In one embodiment, the system 100 includes a base station 415 operative to communicate, via a wired or wireless connection 410, with each piece of exercise equipment 501. The connection 410 may be implemented using a proprietary or non-proprietary communication medium and/or protocol, including Ethernet, Modbus, 802.11, Bluetooth, Zigbee, or other wired, radio frequency, optical or acoustic medium and is implementation dependent. The base station may be implemented as first logic 112 stored in the memory 110 and executable by the processor 108 to cause the processor 108 to receive usage metric data, indicative of the current utilization of each piece of exercise equipment, while the piece of exercise equipment is being utilized, i.e. substantially in real time, e.g. subject to processing and transmission delay, etc. The usage metric data may comprise any measure indicate of the usage, such as power, distance, calories, etc. as will be described in more detail below. The usage data may be received in the form of data packets, described in more detail below with respect to FIG. 8, which include data, e.g. sample data, representative of usage, e.g. cumulative, instantaneous, or otherwise, for or over a period of time. In one embodiment, the usage metric data may be received from the equipment 501 suitably configured to collect and provide the requisite data in the prescribed format. Alternatively, or in addition thereto, sensor nodes 502, as described below, may be affixed or otherwise connected to exercise equipment 501 which is incapable or not configured to provide the usage metric data as described, such as exercise equipment 501 having less functional electronic management systems, or purely mechanical exercise equipment 501 such as mechanical stationary bicycles, human powered cardio machines, weight lifting or other anaerobic exercise equipment. The sensor nodes 502 may be utilized to retrofit such exercise equipment and render it compatible with the system 100 by generating usage metric data, e.g. by extracting or otherwise measuring usage, and providing that usage metric data to the system 100 as described.

The system 100 further includes an aggregator 420 coupled with the base station 415. The aggregator 420 may be implemented as second logic 114 stored in the memory 110, or a different memory separate therefrom, and executable by the processor 108, or a different processor separate therefrom but in communication therewith, to cause the processor 108, or separate processor, to aggregate, e.g. form, group, cluster or otherwise collect or gather, the received usage metric data for each piece of exercise equipment as it is received by the base station, addressably combine the aggregated received usage metric data for each piece of exercise equipment and broadcast the addressably combined aggregated received usage metric data over a network 520, wherein one or more devices, such as displays 435, mobile devices 510, e.g. smartphones 425, tablet computers, and/or other data consumers, etc. coupled thereto may access aggregated received usage metric data of one or more particular pieces of exercise equipment of the plurality of pieces of exercise equipment from the broadcasted addressably combined aggregated received usage metric data. Each aggregate of received usage metric data from a particular piece of exercise equipment may be a metric stream, i.e. a substantially continuous time series of data values representing real time or on-going usage of the particular piece of equipment. As such, the addressably combined aggregated received usage metric data may be composed of multiple decentralized metric streams 440 as will be described.

It will be appreciated that the first and second logic 112, 114 may be implemented as computer readable instructions stored, for example, in the memory 110. It will be appreciated that the system 100 may further include suitable wired and/or wireless interfaces, e.g. network interfaces, radios, etc., not shown, for interconnecting with the exercise equipment 501 and the devices 506, described in more detail below.

The usage metric data may be periodically or continuously received from each piece of exercise equipment 501. For example, the base station 415 may be operative to poll each piece of exercise equipment 501 to request usage metric data therefrom. Alternatively, each piece of exercise equipment 501 may push usage metric data to the base station 415, either synchronously or asynchronously. In one embodiment, wherein a particular piece of exercise equipment is not being used, no data may be received therefrom. Alternatively, unused equipment 501 may send data indicative that the equipment is available or otherwise operational, e.g. a status or heartbeat message.

Generally, the base station 415 may communicate with each piece of exercise equipment 501 using a first protocol, such as a proprietary or non-proprietary wireless protocol, e.g. the wireless protocol described below, whereas the aggregator 420 may broadcast the addressably combined aggregated received usage metric data in a second protocol different from the first protocol. In one embodiment the addressably combined aggregated received usage metric data comprises a data stream formatted according to the User Datagram Protocol ("UDP") multicast format which enables interested devices 506 to substantially simultaneously access any of the usage metric data from the addressably combined aggregated received usage metric data.

To facilitate device 506 access to the addressably combined aggregated received usage metric data, in one embodiment, each piece of exercise equipment may be assigned a unique identifier, such as a UDP port number, the unique identifier used to address the aggregated received usage metric data received therefrom in the addressably combined aggregated received usage metric data wherein any of the one or more devices may access the aggregated received usage metric data of a particular piece of exercise equipment from the broadcasted addressably combined aggregated received usage metric data based on the unique identifier assigned to the particular piece of exercise equipment. In one embodiment, the one or more devices may access only the aggregated received usage metric data of interest and ignore aggregated received usage metric data of the remaining pieces of exercise equipment of the plurality of pieces of exercise equipment.

The network 520 over which the addressably combined aggregated received usage metric data is broadcasted may be a public, private, wired or wireless network utilizing a suitable proprietary or non-proprietary network. In one embodiment, the network 520 is a private subnet utilizing the UDP/TCP protocol which is dedicating to carrying the addressably combined aggregated received usage metric data, for example, so as to avoid congestion on other networks.

Figure 2:
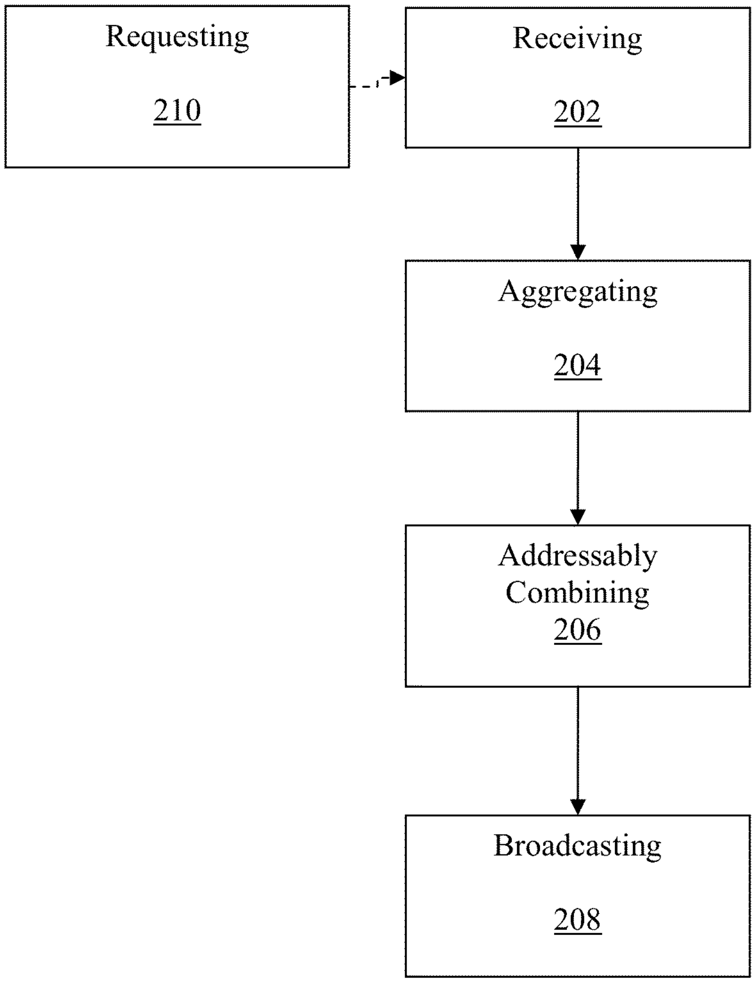
FIG. 2 depicts a flow chart showing operation of the system of FIG. 1.

FIG. 2 depicts a flow chart showing operation of the system 100 of FIG. 1. In particular FIG. 2 shows a computer implemented method for monitoring usage of a plurality of pieces of exercise equipment 501 which includes: receiving, by a processor 108, e.g. via a wired or wireless network 410, periodically or continuously, usage metric data, indicative of the current utilization of each piece of exercise equipment 501, while the piece of exercise equipment 501 is being utilized (Block 202), e.g. substantially in real time, from the equipment 501 directly or via a sensor node 502 suitably affixed thereto; aggregating, by the processor 108 or a different processor coupled therewith, the received usage metric data for each piece of exercise equipment 501 as it is received (Block 204), e.g. into a collection or stream such as a decentralized metric stream; addressably combining, by the processor 108 or a different processor, e.g. based on a unique UDP port numbers assigned and addresses to each piece of exercise equipment 501 or to UDP groups, the aggregated received usage metric data for each piece of exercise equipment 501 (Block 206), such as in the UDP multicast format; and broadcasting, by the processor 108 or a different processor, the addressably combined aggregated received usage metric data over a network 520 (Block 208), such as a private sub-network dedicated therefor; and wherein one or more devices 506, such as display devices 435, mobile devices 510, e.g. smartphones 425 or tablet devices, or other data consumers, coupled thereto may access, e.g. selectively and/or substantially simultaneously, the aggregated received usage metric data of one or more particular pieces of exercise equipment 501 of the plurality of pieces of exercise equipment 501 from the broadcasted addressably combined aggregated received usage metric data, such as based on the uniquely assigned UDP port number.

In one alternative implementation, the operation of the system 100 further includes requesting, by the processor, usage metric data from each piece of exercise equipment, the received usage metric data being responsive to the request (Block 210).

Figure 3:
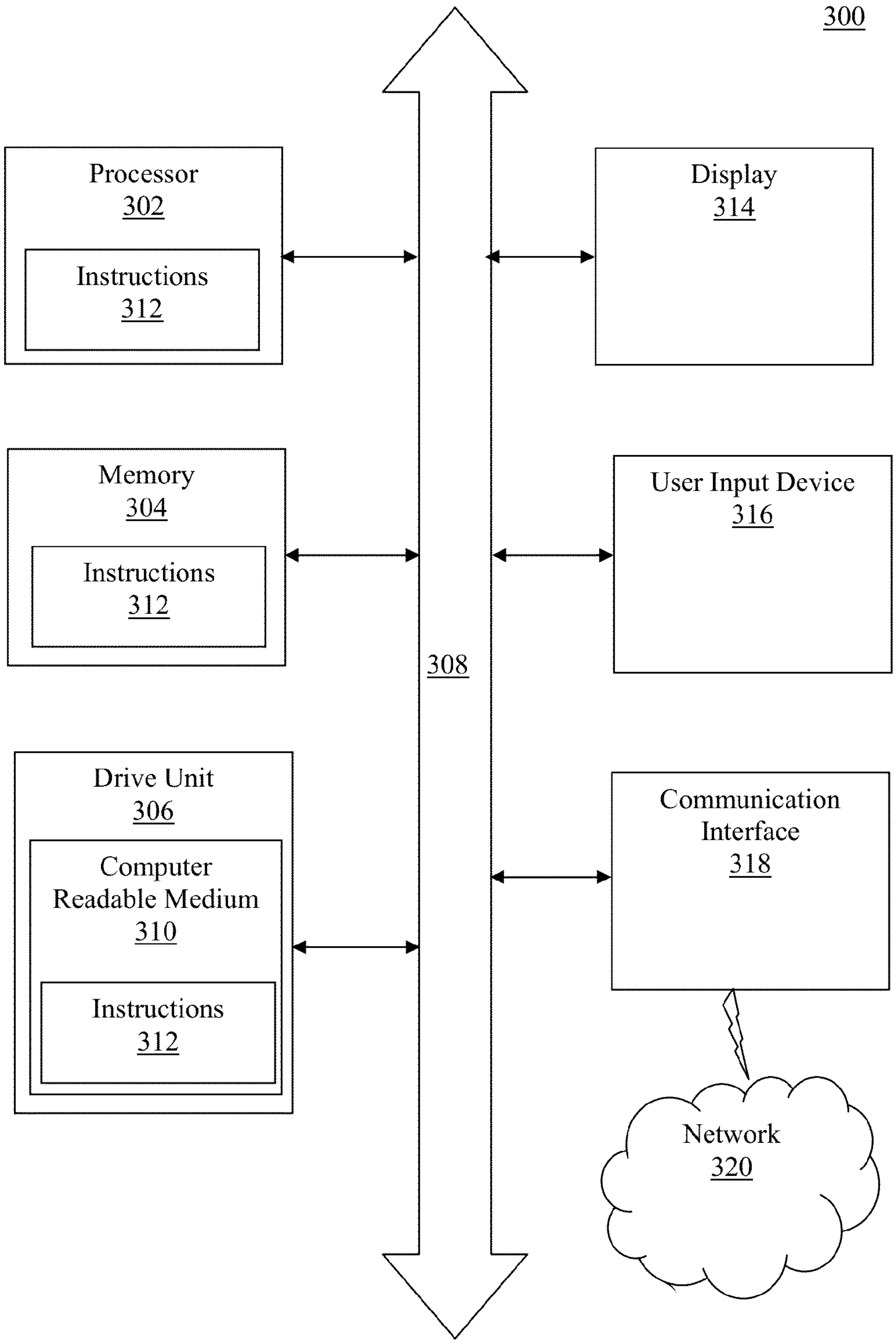
FIG. 3 shows an illustrative embodiment of a general computer system for use with the system of FIG. 1.

Referring to FIG. 3, an illustrative embodiment of a general computer system 300 is shown. The computer system 300 can include a set of instructions that can be executed to cause the computer system 300 to perform any one or more of the methods or computer based functions disclosed herein. The computer system 300 may operate as a standalone device or may be connected, e.g., using a network, to other computer systems or peripheral devices. Any of the components discussed above, such as the processor 108, may be a computer system 300 or a component in the computer system 300. The computer system 300 may implement a system, of which the disclosed embodiments are a component thereof.

In a networked deployment, the computer system 300 may operate in the capacity of a server or as a client user computer in a client-server user network environment, or as a peer computer system in a peer-to-peer (or distributed) network environment. The computer system 300 can also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine In a particular embodiment, the computer system 300 can be implemented using electronic devices that provide voice, video or data communication. Further, while a single computer system 300 is illustrated, the term "system" shall also be taken to include any collection of systems or sub-systems that individually or jointly execute a set, or multiple sets, of instructions to perform one or more computer functions.

As illustrated in FIG. 3, the computer system 300 may include a processor 302, e.g., a central processing unit (CPU), a graphics processing unit (GPU), or both. The processor 302 may be a component in a variety of systems. For example, the processor 302 may be part of a standard personal computer or a workstation. The processor 302 may be one or more general processors, digital signal processors, application specific integrated circuits, field programmable gate arrays, servers, networks, digital circuits, analog circuits, combinations thereof, or other now known or later developed devices for analyzing and processing data. The processor 302 may implement a software program, such as code generated manually (i.e., programmed).

The computer system 300 may include a memory 304 that can communicate via a bus 308. The memory 304 may be a main memory, a static memory, or a dynamic memory. The memory 304 may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one embodiment, the memory 304 includes a cache or random access memory for the processor 302. In alternative embodiments, the memory 304 is separate from the processor 302, such as a cache memory of a processor, the system memory, or other memory. The memory 304 may be an external storage device or database for storing data. Examples include a hard drive, compact disc ("CD"), digital video disc ("DVD"), memory card, memory stick, floppy disc, universal serial bus ("USB") memory device, or any other device operative to store data. The memory 304 is operable to store instructions executable by the processor 302. The functions, acts or tasks illustrated in the figures or described herein may be performed by the programmed processor 302 executing the instructions 312 stored in the memory 304. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

As shown, the computer system 300 may further include a display unit 314, such as a liquid crystal display (LCD), an organic light emitting diode (OLED), a flat panel display, a solid state display, a cathode ray tube (CRT), a projector, a printer or other now known or later developed display device for outputting determined information. The display 314 may act as an interface for the user to see the functioning of the processor 302, or specifically as an interface with the software stored in the memory 304 or in the drive unit 306. A tactile output may further be provides such a mechanical or piezoelectric vibration motor.

Additionally, the computer system 300 may include an input device 316 configured to allow a user to interact with any of the components of system 300. The input device 316 may be a number pad, a keyboard, or a cursor control device, such as a mouse, or a joystick, touch screen display, remote control, accelerometer, motion sensor, proximity sensor, optional sensor, e.g. a camera, or any other device operative to interact with the system 300.

In a particular embodiment, as depicted in FIG. 3, the computer system 300 may also include a disk or optical drive unit 306. The disk drive unit 306 may include a computer-readable medium 310 in which one or more sets of instructions 312, e.g. software, can be embedded. Further, the instructions 312 may embody one or more of the methods or logic as described herein. In a particular embodiment, the instructions 312 may reside completely, or at least partially, within the memory 304 and/or within the processor 302 during execution by the computer system 300. The memory 304 and the processor 302 also may include computer-readable media as discussed above.

The present disclosure contemplates a computer-readable medium that includes instructions 312 or receives and executes instructions 312 responsive to a propagated signal, so that a device connected to a network 320 can communicate voice, video, audio, images or any other data over the network 320. Further, the instructions 312 may be transmitted or received over the network 320 via a communication interface 318. The communication interface 318 may be a part of the processor 302 or may be a separate component. The communication interface 318 may be created in software or may be a physical connection in hardware. The communication interface 318 is configured to connect with a network 320, external media, the display 314, or any other components in system 300, or combinations thereof. The connection with the network 320 may be a physical connection, such as a wired Ethernet connection or may be established wirelessly as discussed below. Likewise, the additional connections with other components of the system 300 may be physical connections or may be established wirelessly.

The network 320 may include wired networks, wireless networks, or combinations thereof. The wireless network may be a cellular telephone network, an 802.11, 802.16, 802.20, or WiMax network. Further, the network 320 may be a public network, such as the Internet, a private network, such as an intranet, or combinations thereof, and may utilize a variety of networking protocols now available or later developed including, but not limited to TCP/IP based networking protocols.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. While the computer-readable medium is shown to be a single non-transitory medium, the term "computer-readable medium" includes a single non-transitory medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein. The computer readable medium can be a machine-readable storage device, a machine-readable storage substrate, a memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

Although the present specification describes components and functions that may be implemented in particular embodiments with reference to particular standards and protocols, the invention is not limited to such standards and protocols. For example, standards for Internet and other packet switched network transmission (e.g., TCP/IP, UDP/IP, HTML, HTTP, HTTPS) represent examples of the state of the art. Such standards are periodically superseded by faster or more efficient equivalents having essentially the same functions.

Accordingly, replacement standards and protocols having the same or similar functions as those disclosed herein are considered equivalents thereof.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

As used in this application, the term ‘circuitry’ or ‘circuit’ refers to all of the following: (a) hardware-only circuit implementations (such as implementations in only analog and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and (c) to circuits, such as a microprocessor(s) or a portion of a microprocessor(s), that require software or firmware for operation, even if the software or firmware is not physically present.

This definition of ‘circuitry’ applies to all uses of this term in this application, including in any claims. As a further example, as used in this application, the term “circuitry” would also cover an implementation of merely a processor (or multiple processors) or portion of a processor and its (or their) accompanying software and/or firmware. The term “circuitry” would also cover, for example and if applicable to the particular claim element, a baseband integrated circuit or applications processor integrated circuit for a mobile phone or a similar integrated circuit in server, a cellular network device, or other network device.

Processors suitable for the execution of a computer program include, by way of example, both general and special purpose microprocessors, and anyone or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a device having a display, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (“LAN”) and a wide area network (“WAN”), e.g., the Internet.

The computing system can include clients and servers. A client and server are generally remote from each other and typically interact through a communication network. The relationship of client and server arises by virtue of computer programs running on the respective computers and having a client-server relationship to each other.

Figure 4:
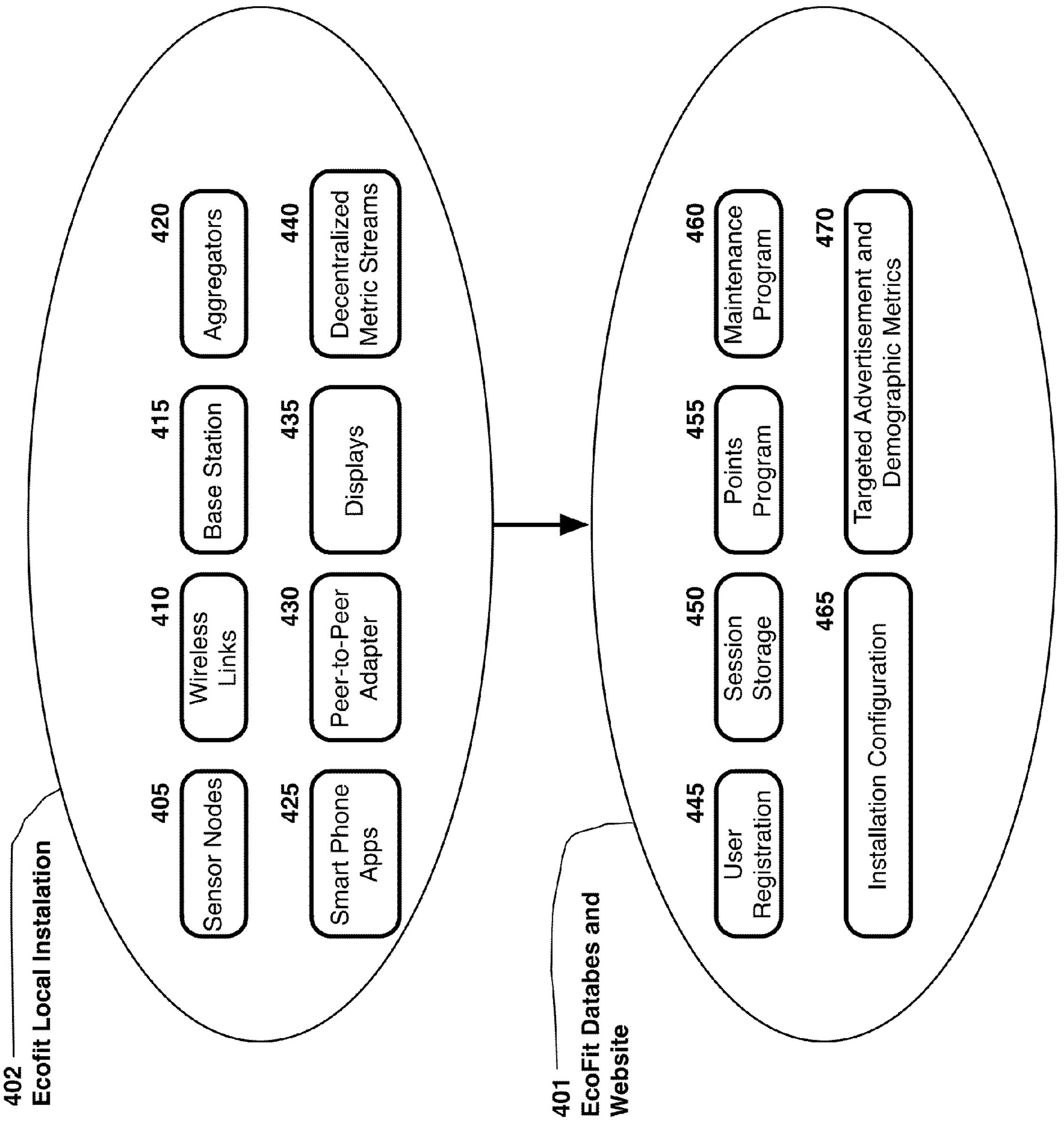
FIG. 4 depicts a logical representations of an exemplary implementation of an exercise usage monitoring system using the system of FIG. 1.

Referring now to FIG. 4, a logical representations of an exemplary implementation of an exercise usage monitoring system is illustrated, which may be referred to as the “ECOFIT system”, which is a data extraction and utilization solution targeted to fitness equipment. In one embodiment, it has a focus on energy producing “green” systems such as the SportsArt Green System, manufactured by SportsArt Fitness located in Taiwan, Republic of China The ECOFIT system is composed of on-the-floor facility installations (ECOFIT Local Installations 402) and a web presence driven by a database to store extracted data 401. The ECOFIT Local Installation 402 is abstracted from the type of exercise equipment it is extracting data from at the source using ECOFIT Sensor Nodes 405. After the sensor nodes 405, any data extracted is carried on the ECOFIT Wireless Link 410 to data receivers (ECOFIT Base Stations 415 paired with Aggregators 420) and converted to ECOFIT Metrics, which can be made use of in real-time or substantially real-time at the local installation using ECOFIT Displays 435 and smart phone applications 425. It should be appreciated that an ECOFIT Display 435 may be any typical display, such as the display 314 described above with respect to FIG. 3, which enables a user to view display information from a connected device. The metrics and are pushed up to the ECOFIT Database 401 for further metric extraction and storage for later use. The ECOFIT Local Installation 402 may further include Peer to Peer adapter 430 capabilities and decentralized metrics streams 440.

The components of the ECOFIT Website and Database 401 allow for configuration of components of the ECOFIT Local Installations 402 as well as user session review, user registration to become ECOFIT Network members 445, and other value-added functionality such as data session storage 450 for the user. While the database is primarily for user session storage, it is also used in concert with the website to make available the ECOFIT Maintenance Program 460 and the ECOFIT Points Program 455. Statistics are also made available to advertisers and other interested parties through the ECOFIT Database and Website via a targeted advertisement based on demographic metric 470 which may also be delivered through ECOFIT installation displays. These features are made available mostly through the website using function-specific portals for different types of users (ECOFIT members, facility owners, equipment manufacturers etc.). In addition, the Website and Database 402 capabilities may also provide Installation Configuration 465 capabilities for a facility owner.

ECOFIT Local Installation

Figure 5:
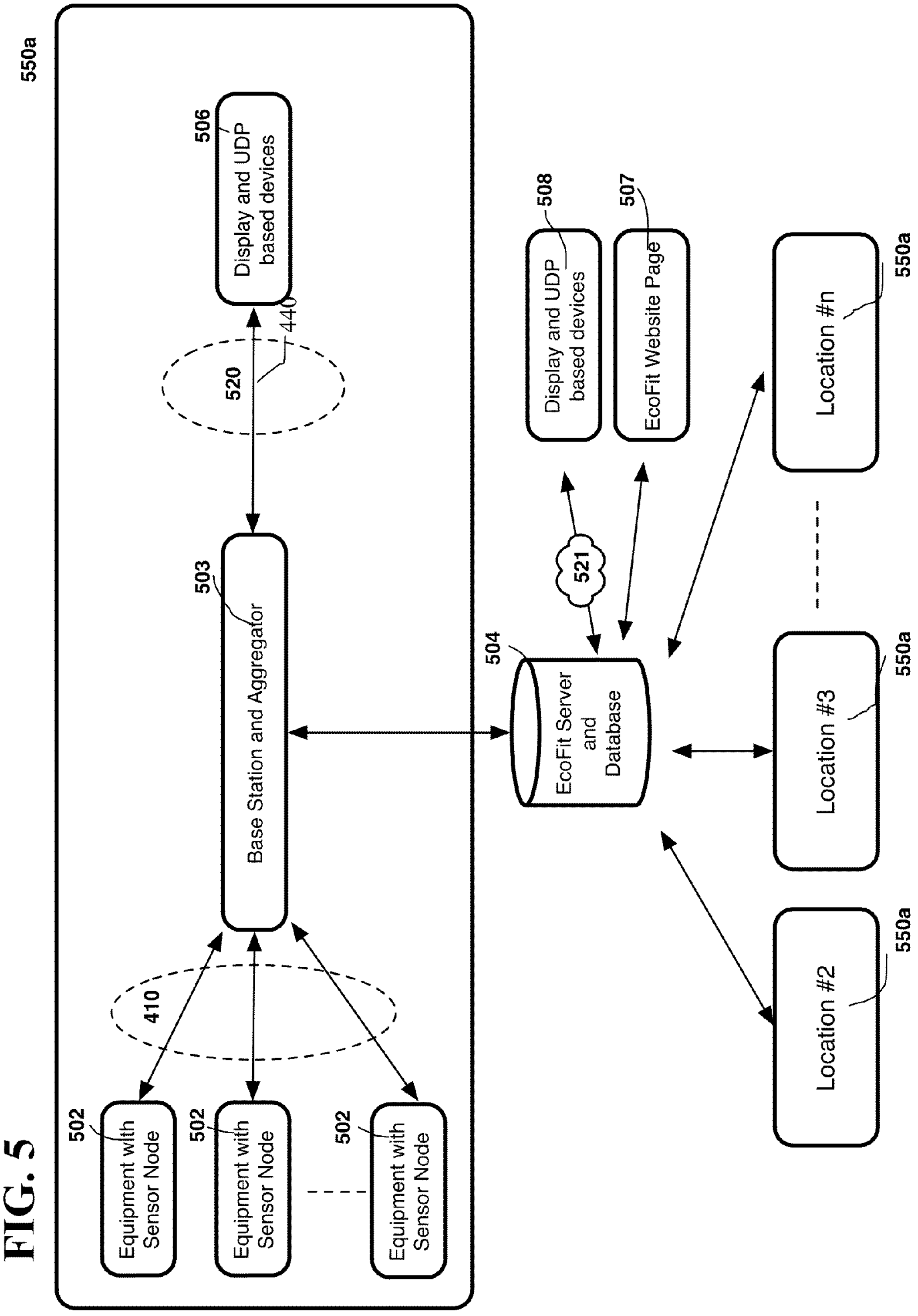
FIG. 5 depicts an exemplary architecture of an ECOFIT exercise usage monitoring installation according to one embodiment.

Referring now to FIG. 5, an exemplary architecture of an ECOFIT exercise usage monitoring installation according to one embodiment is illustrated. Local sub-systems 550*a*, which can be physically located in the same fitness facility or at separate locations, generally include various pieces of exercise equipment each fitted with a sensor node 502, which communicates with a Base Station and Aggregator components 503. The Base Station and Aggregator components 503 communicates both with an external, e.g. ECOFIT, server and database 504 via a network, such as the Internet, as well as displays and other UDP based devices 506, via a local network 520, such as a dedicated subnet. A wireless link or network 410 enables the equipment and sensors nodes 502 to communicate with the Base Station and Aggregator components 503, whereas a separate communications network 520 allows for the Base Station and Aggregator components 503 to communicate to other UDP based devices. In operation the network 410 utilizes a protocol that may enable communication of standardized data to the Base Station and Aggregator components 503, and the network 520 may be an open protocol network, such as UDP, UDP Multicast, JSON-RPC over TCP, TLS, web sockets, etc., which may allow any user or facility device to be configured easily with standard software programs in order to receive and display the data.

In one embodiment, the ECOFIT installation is supported with a single router to create a subnet inside a local installation 550 where real-time metrics from equipment can be collected and disseminated, equipment containing Sensor Nodes 502, Aggregators and Base Stations 503 to collect metrics, Displays to display metrics 506 and may also include Inverters to feed generated power from power generating equipment back to the power grid (not shown).

Figure 6:
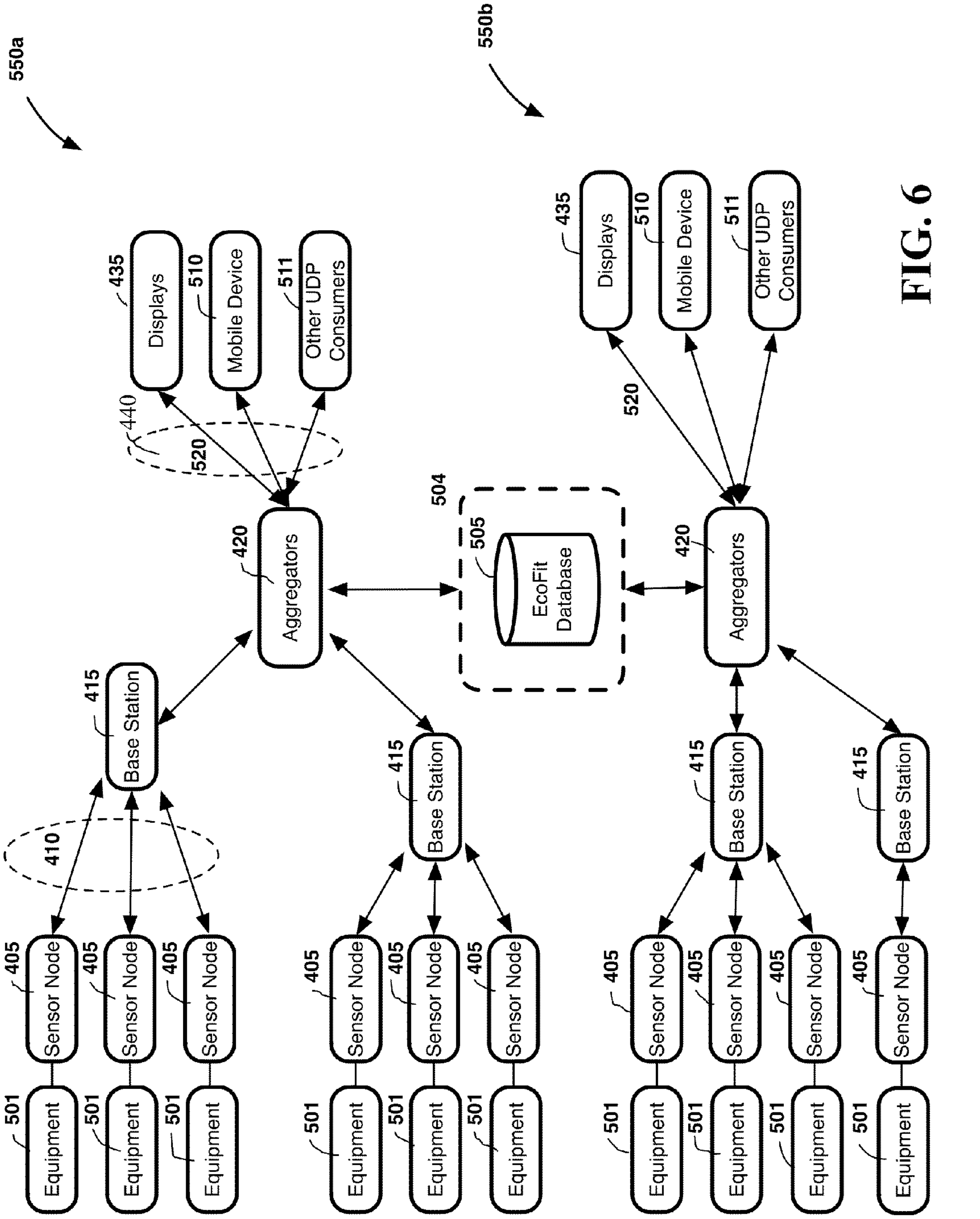
FIG. 6 depicts the device details of an exemplary implementation of a local installation of the architecture shown in FIG. 5.

Referring now to FIG. 6, a detailed architecture of the ECOFIT System is illustrated. The equipment portion of an ECOFIT Local Installation 550 consists of fitness equipment 501 and inverters which include either coupled to or embedded within them ECOFIT Sensor Node 405. The ECOFIT system is configured to allow for easy customization to variable equipment communication protocols and metric interpretation. Equipment can be power generating (for example for feed power back to the grid through an inverter), self-powering (for example removing the need for an external power supply but also not feeding power back into the grid) and powered (for example, requiring a power supply, but not feeding power generated back into the grid.).

Sensor Node

The Sensor Node 405 is a combination of a wireless radio and an ID reader with a protocol module responsible for communicating with the underlying fitness equipment and extracting manufacturer-specific metrics. ID readers may include a RFID (Radio Frequency Identification), a Quick Response ("QR") Code reader or another reader based technology that may be used to personally identify a user of the exercise equipment. The protocol module will implement the appropriate communication protocol for the equipment, such as the ANT, ANT+ or CSAFE protocol, and may be done over a wireless communications medium such as RF, Bluetooth low energy, or a other wired medium, or a combination of both mediums. The metrics extracted from the equipment is defined by the installation configuration and can be changed as new metrics are needed.

In one embodiment of the invention the ID reader portion of a Sensor Node 405 is responsible for reading the unique ID of the ECOFIT RFID member card when a user begins a session on the equipment 501. This unique ID is transmitted by the Sensor Node 405 over the Wireless Link 410 or network to the Base Station 415 and Aggregator 420 and then relayed to the ECOFIT Database 505 where the user's name is extracted and returned. This user name can then be used at the Local Installation 550 for various purposes such as labeling the user's real-time metric feed on a Display 435 in the facility. Alternately the user name is read directly from the ID card and used at the Local Installation 550, ensuring the user may immediately begin a session and have their name displayed on a Display 435 even if communications to the ECOFIT Database 505 is interrupted.

Dropping the ID card onto a piece of equipment starts a session, removing the card ends the session. In one embodiment where a proximity card is utilized, such as a RFID card, the login and logout is done automatically. In an alternate embodiment where a user scanning login/logout is utilized, such as with a QR code, the user may logout to close the session or it may be done automatically using a defined timeout of inactivity or non-utilization of the equipment 501, as detected by ECOFIT system.

The Base Station 415 contains a wireless transceiver that polls its associated Sensor Nodes 405, over the Wireless Link 410, and communicates to receive metrics from the Sensor Nodes 405. The Base Station 415 is also responsible for initial identification of its Sensor Nodes 405 and assigning these nodes their frequency channels.

Base Station

The Base Station 415 may include a storage memory, such as memory 304, which is configured to store configuration data for the ECOFIT system or hold commands in memory until can be forwarded to the Sensor Nodes 405. It will be appreciated that the Base Station 415 and Aggregator 420 may be provided as separate devices for an installation, or as a combined device for ease of use and installation by the facility.

Wireless Link

The Wireless Link 410 creates a communication network with the use of a radio module relaying data from the Sensor Node 405 to a Base Station 415. Each Sensor Node 405 is associated to a single Base Station 415 according to the installation configuration.

The Wireless Link 410 implements a frequency hopping scheme to allow for reduced interference from other RF sources. In one embodiment the Wireless Link 410 communicates data in a proprietary protocol, and in an alternate embodiment in a standard or open protocol. The frequency hopping scheme operates via two radios on the Base Station 415, where radio 1 is used to collect metrics from Sensor Nodes 405 and radio 2 is used to identify Sensor Nodes 405 that have lost sync with the Base Station 415. The process which the Sensor Node 405 moves the data via the Wireless Link 415 is described below:

- Radio 1 in the Base Station 415 sends sync packet to Sensor Node 405 containing the Sensor Node ID and the next 10 channels in the frequency hopping array.
- Sensor Node 405 uses auto acknowledge with payload to return data to the Base Station 415. If the Sensor Node 405 has more than 1 packet worth of data, it requests the Base Station 415 send another transmission to transfer the additional data.
- After each sample is sent or time expires the Sensor Node 405 moves to the next channel in the channel array.
- If the Sensor Node 405 reaches the end of the channel array after having timed out ten times (ten seconds without Base Station connectivity) the Sensor Node jumps to one of the base channels to regain sync from radio 2.
- To regain synchronization, there are three base channels which the system uses (one low channel, one medium channel, one high channel to avoid possible interference). The Sensor Node 405 spends ⅓ of a second on each channel waiting for the Base Station 415 to tell it what channel to go to.
- Radio 2 sends the Sensor Node IDs and the current channel they should be on for each Sensor Node 405 which is missing on each of the three base channels once per ⅓ of a second (3 times per second on each base channel, 9 transmissions total).
- When the Sensor Node 405 hears its ID and channel it jumps to the channel and waits for a timeframe, 1 second, for radio 1 to ask for its data. If it does not hear radio 1 within this timeframe it returns to the base channel to get the next channel to move to.

Aggregator

The Aggregator 420, which may be implemented in software which may reside on a computer system, such as the computer system 300 described above with respect to FIG. 3, may be combined with or paired to one or more Base Stations 415. It is responsible for receiving the metrics which the Base Station 415 captures from Sensor Nodes 405. The metrics are then processed to ECOFIT metrics, which may provide a standard metric system to compare and communicate data over the system. Once the received metrics are converted into ECOFIT metrics, they are streamed via UDP multicast over the network 520 for consumption by players and any other devices that may connect to a UDP multicast or other internet based readers, such as displays, tablets or smartphones.

Each Aggregator 420 is assigned a UDP multicast IP address while each piece of equipment 501 (identified by equipment ID residing on the Sensor Node 405) associated with that Aggregator 420 is assigned a UDP port number from 1025 up. In this arrangement, a metrics consumer need only be connected to the local network, such as the network 520, and know the multicast IP address and port number of the piece of equipment it needs to consume metrics from and a real-time socket may be created. The data is buffered at the Aggregator 420 as a session and when a session is complete it may be relayed to the ECOFIT Database 505. As described in detail below, the session may not be forwarded to the ECOFIT Database 505 until a session is complete.

Figure 7:
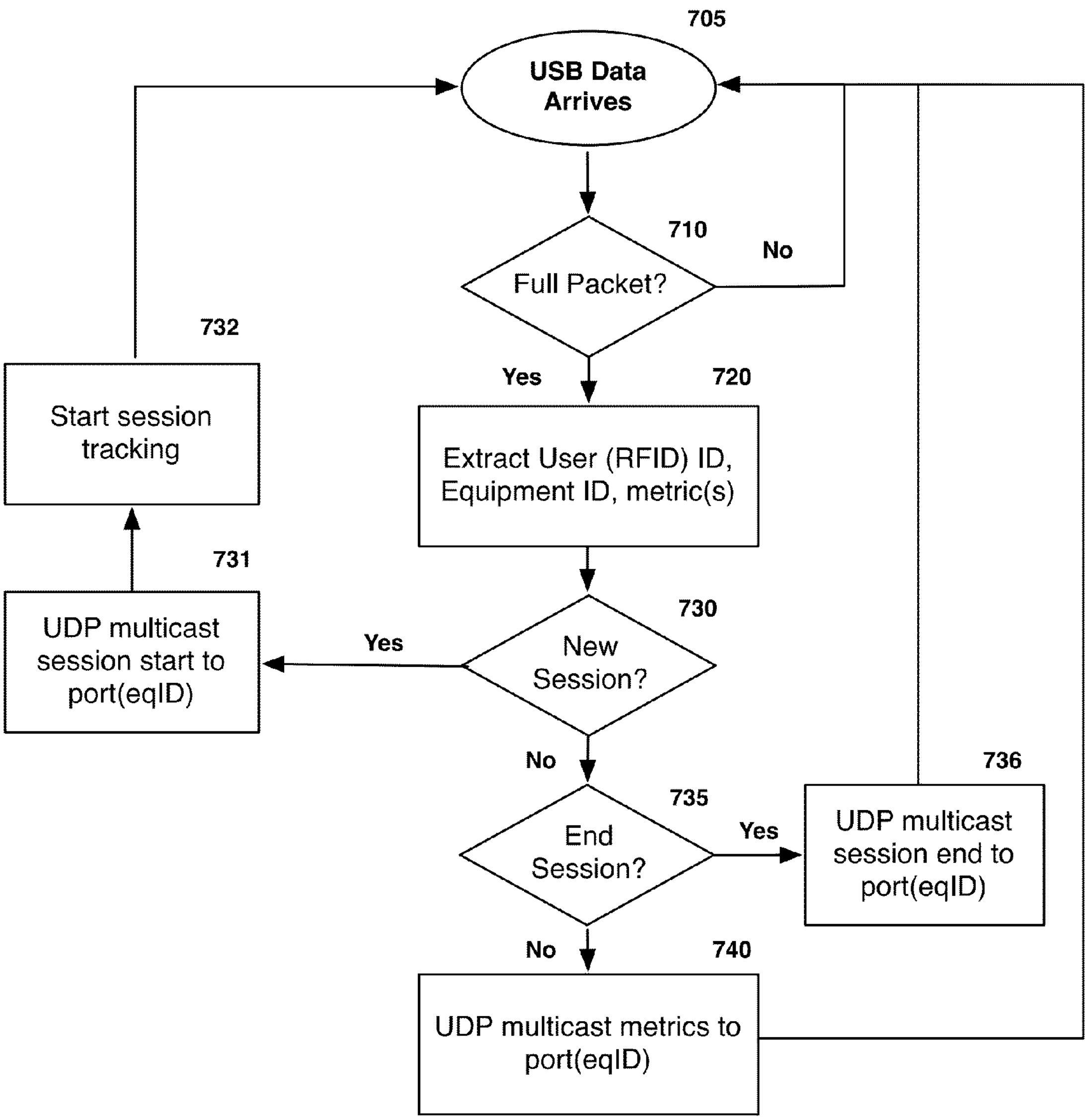
FIG. 7 shows a flow chart depicting an exemplary process for buffering the data received by the Aggregator shown in FIG. 5.

Referring to FIG. 7, the process which the Aggregator 420 data is buffered as it is received is described.

When data arrives (block 705) the Aggregator confirms if it is a full packet of data (block 710). If not it continues to collect the data, but once a full packet is noted, the Aggregator extracts the appropriate data, such as the user ID, equipment ID and associated metrics (block 720). If a new session has been identified with the information in the packet (block 730), a UDP multicast session is started (block 731) and then session tracking in the Aggregator 420 is initiated (block 732). If no new session is identified the Aggregator checks to see if the session has ended (block 735) and if not continues to track and record the session, as well as continuously transmit the metrics via UDP multicast (block 740), on the network 520. This allows for any user or device 435 510 511 to receive and display the data as it is being buffered in the Aggregator 420. If the session has ended (block 735) a UDP multicast session end signal (block 736) is sent.

Once the Aggregator 420 identifies that a session has ended it will transmit the data to the ECOFIT Database 505. As will be described later the identification of a session status is included in the data. In operation transmission of the session is relayed via a web protocol, including but not limited to TCP, JSON-RPC over TPC, SOAP, REST or other internet capable protocol, to interface to the ECOFIT Database 505. The Aggregator does not delete the session data until conformation it has been received and stored by the ECOFIT Database 505.

To transfer the session from the Aggregator 420 to the ECOFIT Database 505 a web server based message may be sent, such as via a HTTP Post operation. This allows the message to be formatted in a common way to transmit the data. In operation a HTTP Post sends a string of data which has contains all the sampled data metrics, cumulative aggregate data metrics, and any other relevant data such as a start and stop timestamp for the ECOFIT Database 505 to use. For example a submission from the Aggregator 420 to the ECOFIT Database 505 for a session may be in the form of:

{"aggregateMetrics": {"0000":30.0,"0001":160.9344,"0003":2.0,"0004":11.10447 36,"0005":12.9763947789,"0007":17.702784, "0008":0.0900537959764,"0009":0. 0726179256014, "000B":0.119494460046,"000C":28.0,"000D": 32.1578947368,"0 00F":45.0,"0010":93.0,"0011":91.5, "0013":93.0,"0014":0.2,"0015":0.4210526315 79,"0017": 0.8,"0018":79.9473684211,"001A":154.0,"001B": 14.6842105263,"001 D":64.0,"001E":2.0,"001F": 0.0774472222222,"1000":0.421863611111},"samples": [{"metrics": {"001F":0.0,"0013":90.0,"0015":0.0,"0000": 3.0,"0004":11.9091456,"0009":0.041984540016,"0017": 0.0,"001A":3.0,"001E":0.0,"0005":5.9545728,"0 01D":0.0, "0008":0.0839690800321,"000F":22.0,"0018":1.5,"0007": 11.9091456,"0010":90.0,"000C":22.0,"001B":0.0,"0001": 0.0,"1000":0.000833333333333,"001 1":90.0,"000D":11.0, "0003":0.0,"0014":0.0,"000B":0.0839690800321}, "offset":0 },{"metrics": {"0007":17.702784,"0004": 15.4497024,"0017":0.8,"001A":154.0,"1 000": 0.279301388889,"0001":160.9344,"001F": 0.0560844444444,"001E":21.0,"0 00F":45.0,"000D": 30.5833333333,"0009":0.0700355959491,"000C":40.0, "0013": 92.0,"0015":0.433333333333,"0018": 83.8333333333, "0010":92.0,"0005":12.4992 384,"001D": 64.0,"0000":154.0,"0011":91.0,"0014":0.8,"000B": 0.119494460046,"0003":1.0,"001B":16.8333333333, "0008":0.0647261658581},"offset":10}],"start":"2012-06-19T14:02:48.427","end":"2012-06-19T14:03:08.377", "rfid":"D0020CBF52004860","facility":"8d679177-0d97-42ad-bfc8-23820d977aba","equipment": "000000001546DDAD"}

In another example, retrieval of data from the ECOFIT Database 505 to the Aggregator occurs in the same format. For example, a HTTP Get operation can be used to retrieve member profile data, which may be in the form of:

{"screenName":"Brendan","flags":"0003","rate": {"metricID":"001F","factor":2. 0}}

The Aggregator 420 may be run along side an ECOFIT Display 435 on the same computer, or may located separately.

Display

ECOFIT Displays 435 may include any display unit 315 that displays information or data from the system for a user. In one embodiment the ECOFIT Display 435 is customizable and utilizes commercial digital media technology, such as Broadsign display technology, manufactured by BroadSign International, located in Montreal Canada, as well as a host of internet enabled widgets that may consume from the local network and display real-time metrics from individual pieces of equipment. Internet enabled widgets may include Flash, Silverlight, HTML5 or other formats known in the art. The use of Broadsign display technology allows for full customization of each display, a range of data feeds beyond the ECOFIT local network metrics data (RSS feeds, streaming video). In practice, a display is composed of the Broadsign software which resides on a computer which is paired to a monitor. The display software may reside on the same computer as an Aggregator 420.

Display content can be customized as either an ECOFIT service or through the ECOFIT website by facility owners. Information such as fitness class schedules and competition results can be displayed along-side advertisement campaigns and real-time metric feeds.

Other displays, such as personal displays provided by a users smartphone or tablet 510 511, also can be configured to display customized data for the user, which may include custom applications for a user. In operation smartphone or tablet 510 511 application may connect to the ECOFIT service once the smartphone connects to the network 520, the application configured to scan the network 520 to find the appropriate Aggregator 420 to connect and display the broadcasted data from.

Session

A session starts when a user identifies themselves to the equipment, such as linking their ID card at a piece of equipment or other initiation using an application on their smart device or tablet. While the user is using the equipment, metrics are captured and buffered at the Aggregator 420 via the Base Station 415. When the user removes their RFID card to signal to the Sensor Node that the session it completed the Aggregator sends the buffered session to the Database. In one embodiment the session is defined as a set of captured metrics over the span of a user's use of a piece of equipment and is associated with an ID unique identifier, such as the RFID, a Sensor Node unique identifier and a start and stop time that is relative to the equipment use. In an alternate embodiment a session may be defined as a user that utilizes multiple pieces of equipment, e.g., a "circuit". For a user it may be advantageous to capture metrics from their exercise circuit and have them displayed or stored as one session. In a first example providing a circuit as a single session for a user may be done by accounting for a timespan that may elapse between the stop time of a first session and the start of a second session, which would account for the time required for a user to move between equipment and give the perspective from the user that the session is a continuous session. In a second example the session may be paused by a user. For example a user may begin a session on running equipment and then after completing use on the running machine virtually pause the session, which may occur by removing the RFID card or pausing the session on their smart phone application, and then reinitiating the session by beginning use on a second piece of cycling equipment, which may occur by reapplying the RFID card to the cycling equipment or unpausing the session on their smart phone application. The timespan may be fixed by the facility's configuration of the system, such as 5 minutes, or configured by the user, either allowing adequate time for a user to move between equipment pieces without the session prematurely ending or allow for collection of residual metrics, such as heart-rate monitoring during a users personal cool-down routine. It can be appreciated that extending the timespan to a longer period, such as 1 hour, will allow a user to capture their real-time exercise data across multiple pieces of exercise equipment and ultimately provide them the data in the ECOFIT Database 505 as a general workout, as opposed to providing them as discrete workouts linked to individual pieces of equipment.

Metrics

A metric is a particular measurable value that the ECOFIT system extracts from exercise equipment. In addition the installed system may receive from external equipment, such as Heart Rate Monitors or other personal monitoring equipment. A simple example of a metric is watts. Most modern exercise equipment capture watts generated by a user. The system can extract measured watts and make it available on the ECOFIT Local Installation 550 for real-time consumption as well as to the Database 505 for near real-time web applications and off-line storage for later usage. Because each manufacturer defines their metrics differently, the system includes its own defined list of metrics which can be translated from manufacturer metrics. This allows the system to be easily adapted to any piece of exercise equipment while maintaining an abstracted front-end that appears the same for any underlying equipment.

Table 1.0, below, lists exemplary metrics that may be measured, either directly or calculated virtually over a period of a session, such as averages, maximum or minimum counts, and their associated units of measure. Many of the metrics are generated or measured by equipment, however the Aggregator 420 may also generate metrics which may be needed by the ECOFIT Database 505. For example, a "Duration" metric is generated by the Aggregator 420 and is the duration of the particular number of seconds elapsed since the beginning of a session which enables a display to have an accurate count of the session length which may be displayed for a user.

TABLE 1.0

| Metric Name | ECOFIT ID | Unit of Measure |
|---|---|---|
| Distance Horizontal | 0001 | Meters |
| Distance Vertical | 0002 | Meters |
| Calories | 0003 | Calories |
| Speed (Control and Display Metric) | 0004 | KM/H |
| Speed Average | 0005 | KM/H |
| Speed Minimum | 0006 | KM/H |
| Speed Maximum | 0007 | KM/H |
| Pace | 0008 | H/KM |
| Pace Average | 0009 | H/KM |
| Pace Minimum | 000A | H/KM |
| Pace Maximum | 000B | H/KM |
| Cadence | 000C | RPM |
| Cadence Average | 000D | RPM |
| Cadence Minimum | 000E | RPM |
| Cadence Maximum | 000F | RPM |
| Heart Rate | 0010 | BPM |
| Heart Rate Average | 0011 | BPM |

TABLE 1.0-continued

| Metric Name | ECOFIT ID | Unit of Measure |
|---|---|---|
| Heart Rate Minimum | 0012 | BPM |
| Heart Rate Maximum | 0013 | BPM |
| METS | 0014 | METs |
| METS Average | 0015 | METs |
| METS Minimum | 0016 | METs |
| METS Maximum | 0017 | METs |
| Power | 0000 | Watts |
| Power Average | 0018 | Watts |
| Power Minimum | 0019 | Watts |
| Power Maximum | 001A | Watts |
| Electrical Power | 001E | Watts |
| Electrical Power Average | 001B | Watts |
| Electrical Power Minimum | 001C | Watts |
| Electrical Power Maximum | 001D | Watts |
| Electrical Watt Hours | 001F | Watt Hours |
| Level (Resistance) | 0020 | |
| Grade (Incline) | 0021 | % |
| Utilization | 0022 | Seconds |
| Watt Hours | 1000 | Watt Hours |
| Duration | 1001 | Seconds |
| Points | FFFF | ECOFIT Points |

ECOFIT Local Network

All elements of an ECOFIT Local Installation 550 which produce or consume data do so on the ECOFIT Local Network. In one embodiment this network 410 520 is a subnet behind its own router to avoid bogging down a facility's network, and/or, in another embodiment, it may be operating on the facility or building's own network. UDP multicast from Aggregators 420 for the purpose of real-time availability of user generated metrics is done on this local network and does not extend out to the parent network, i.e., to an external network to the facility. As a result consumption of UDP multicasts is also only done on the ECOFIT Local Network and may not be consumed outside this network.

This subnet enables devices or consumers to connect to the Aggregator 420 to consume the streaming data in real-time.

In an alternate embodiment, the subnet is created with a virtual router, and allows for ease of devices, such as a smartphone device configured to receive ECOFIT metrics, to pair with the Aggregator and consume the data without the need to install a separate hardware based router.

The exception to this is multicast data that is streamed through the Adapter to the external network to allow for facility-to-facility competition. For data that is needed by devices external to the network during a session, such as for facility-to-facility or other peer-to-peer competition, the Adapter may include a second database, referred to as an Uplink Server, hosted at the same location as the ECOFIT database 505 such as on the ECOFIT Server and Database 504. The Uplink Server may act as a virtual Aggregator for inter-facility comparison of data, by receiving data from the Aggregator 420 as it is collected, and then allowing other facilities to consume the data as requested by their display based devices. This enables any device that can connect to the local network 520 to stream any data from the Aggregator 420 in a real-time, or substantially real-time manner. It should be appreciated by one skilled in the art that various protocols can be implemented by the Uplink Server, such as TCP, to communicate the data. In one embodiment the Uplink Server is communicated to in real-time, at the same rate the UDP multicast data is sent from the Aggregator 420. Alternately the Uplink Server is transmitted to on demand, for example only when data from a piece of equipment is requested. This will ensure efficiencies of the network connection and data transfer. To further ensure efficiencies, it should be appreciated that facility-to-facility connectivity and communication may also occur by direct connection of one facility's Aggregator 420 to another facility's Aggregator 420, bypassing the Uplink Server.

The system is designed to easily adapt to new exercise equipment with varying communication protocols and metric definitions. To accomplish, or any required change in the system, a configuration may be done by the facility. ECOFIT Local Installations 550 may be defined at the ECOFIT website 507 where equipment is arranged, necessary IDs (such as unique ID's for equipment 501, Sensor Nodes 405 and Base Stations 415) are assigned and configuration files are generated. The majority of the ECOFIT Local Installation 550 configuration is communicated through the configuration files, which may be generated by the website 507 or the ECOFIT Server and Database 504 which may be on a network external to the local facility. In an alternate embodiment the configuration may be done through direct connection to the ECOFIT Server and Database 504.

There may be two types of configuration files that may be used, and creation of the configuration files will be discussed in detail later. The first is the display configuration which indicates which UDP multicast streams displays or devices should consume, and the second is the configuration files used by the Aggregator 420 and subsequent downstream devices such as the Base Station 415 and Sensor Nodes 405.

In either case the configuration files are pulled down from the web in an open standard format and are parsed at the displays and Aggregators, such as XML, JSON or other format. This web access may be a web-based intranet, extranet or internet based service on a network external to the local location, or via an internal network or server, such as the ECOFIT Server and Database 504 505. Sensor Nodes 405 are associated to Base Stations 415, Base Stations 415 are associated to Aggregators 420, and Displays 435 are associated to equipment 501 (via the Sensor Nodes 405) by these configuration XMLs. UDP multicast IP and port number pairs are associated to equipment, allowing for an addressing scheme on the local network or for the location 550. UDP Groups may also be formed in the configuration file and associated with multiple pieces of equipment, or for one Aggregator. For example, a particular piece of equipment (Sensor Node A) might be associated to multicast IP 224.0.0.100 port 1025. If a display needs to consume metrics from Sensor Node A, its configuration file will include a look-up table with an entry for Session Node A indicating that the metrics can be extracted by connecting to multicast IP 224.0.0.100 port 1025. The Aggregator 420 responsible for producing Sensor Node A's metrics will have obtained its multicast IP 224.0.0.100 from its configuration file and will have also been instructed to make available on UDP port 1025 the metrics extracted from the wireless link for Sensor Node A.

In one embodiment the configuration file is pushed to the Aggregator 420, which then distributes the configuration file to all devices (Base Stations 415, Sensor Nodes 405, etc.) that are connected downstream of the Aggregator 420. Alternately an Aggregator 420 polls or queries the ECOFIT Database and Server 504 for a new configuration file.

Figure 8:
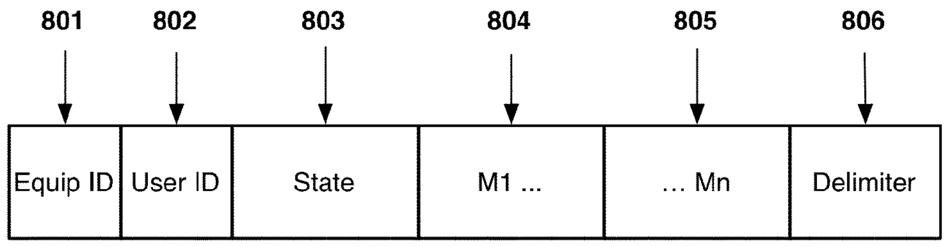
FIG. 8 illustrates a logical structure of an exemplary packet received by the Aggregator shown in FIG. 5.

Configuration files are also responsible for defining which metrics a Display 435 or any other UDP based consumer 510 511 is interested in consuming. Since manufacturers have varying definitions of metrics and varying communication protocols, the configuration files also need to contain information that the Sensor Node 405 may use to extract these metrics. Configuration files that are parsed and transmitted over the Wireless Link 410 to a Sensor Node 415 contain lists of metric IDs associated to protocol commands to extract those metrics as well as expected response length. This allows for great variability in protocol and metric definition. FIG. 8 illustrates a diagram of an exemplary packet received by the Aggregator 420. Once the configuration file has used to configure the Aggregator 420 and the devices coupled to it, for example the Base Station 415, the aggregator can simply receive and parse a packet of data.

Referring in detail to FIG. 8, the configured packet 800 may include an Equipment ID field 801, a User ID field 802, a State field 803, several metric fields 804 805, and a delimiter field 806. It will be appreciated that the logical structure of the data packet, both in terms of the fields included therein, the format of the data, the arrangement of the fields, etc. is implementation dependent. For example the Equipment ID field 801 may be a 16 byte field that allows for the unique ID of a piece of exercise equipment 501 and the User ID field 802 also a 16 byte field that allows for a unique ID of a user, such as a RFID code, both of which are definable pieces of data. The State 803 may be a 2 byte field that allows for four states, such as 0 "Equipment on, no session, metrics", 1 "Equipment on, new session, metrics", 2 "Equipment on, session going, metrics", or 3 "Equipment off, no metrics". Referring back to FIG. 7, block 730, in operation the State field 803 allows the Aggregator 420 to know when to stop or start a new session. There may also be flags associated with each of the States to identify for the Aggregator 420 other commands to execute on when managing the data, such as erasing or making anonymous certain user data fields for privacy or reporting issues. The metric fields 804 relate to the specific metrics expected to be monitored by the exercise equipment 501, as defined by the configuration file. The configuration file ensures metrics fields 804 805 are formatted in consistent byte length so the Aggregator 420 can read and understand a particular value of incoming packet based on its position in the packet itself without the need to have an identifier or tag (i.e., "Speed Metric" at the start of each packet's field). In one embodiment the packet delimiter field 806 may be included in the packet to identify the completion of the packet. In an alternate embodiment the delimiter field 806 may not be required as the configuration file may define the number of metrics to be read, and thus the Aggregator 420 will not need to continue to parse a captured packet once the last data piece of the expected 'n' pieces of definable data has been received.

As described earlier for each Aggregator 420, these 'raw' metrics are converted to ECOFIT metrics using processes which are associated to the metric ID. Examples of the metrics and associated ECOFIT metric ID's are shown in Table 1.0. These processes are also contained within the configuration file that the Aggregator 420 retrieves from the aforementioned website or other networks.

As described earlier, a display or associated UDP consumer device may require a different configuration file, and thus packet sent to such a display contains the same data as the sample described above, along with specific definable data needed, such as equipment and user ID data. This allows a display to acquire a session at any time and immediately know the status of that session. In addition the packet in this example may also include a status indicator which tells the display if a user is in the middle of a workout or if the equipment is at idle.

Website and Databases

The ECOFIT Database system 504 is a relational database designed to store a variety of data points captured from sources referred to as "Equipment". Data is captured in the system as periods of activity, known as "Sessions", these sessions store all definable points of data.

These points of definable data include:

Which piece of equipment this data was captured from;

Where the session occurred (A "Location");

Which identification card was used to register a session;

The data points captured during the session.

This system defines captured data by metrics, which are a combination of a common name (Example: Watts), a unit of measurement (Example: W), what type of data the metric is (Example: String, Int, Floating Point), and whether the data can be aggregated. These metrics are used to record data at both the session level (aggregated session metrics) and at the "Sample" level. Samples are individual points of time within a given session, specified as a particular number of seconds since the beginning of a session, such as the "Duration" metric. Metrics can record any point of consumer or exercise data that is needed, as long as it can be defined by a name, unit, and type of data.

For example, each data packet that is sent from the Aggregator 420 to the ECOFIT Database 505 may contain a full definition of cardio session that a user is experiencing. This data may include a header with the definable points of data, an aggregate metric packet which contains the final values for all metrics for the session (as paired metric IDs and values), and a complete set of samples, as described earlier. Each sample for the workout may include one or more offset values, which is the number of seconds from the start of the session that the sample occurred at (for example counted in 10 second increments, i.e., 0, 10, 20, 30 . . . ), as well as it's own set of metric ID/value pairs. The offset value may be generated into the stored sample dataset by the Aggregator 420. These sets of metrics may vary from packet to packet, allowing unchanged or unnecessary values to be left out of individual samples to reduce the wire size of the pack.

In one embodiment samples are transmitted, polled or received from the Sensor Node 405, such as every 10 seconds, for the duration of the session. This example timeframe of 10 seconds may be decreased or increased to match the appropriate sampling rate that corresponds with the monitoring needs and still takes into consideration the bandwidth limitations of the any networks 320 410 520. For example, for many equipment users sampling greater than 10 seconds may not yield a large variation in measured metrics (i.e., average, minimum, maximum) thus sampling at a greater rate will only increase the volume of metrics transferred over the wireless link 410 yet yield no measurable viewing of results for a user. In an alternate embodiment the samples are generated or received at a greater rate, where a facility may be providing a higher resolution of information to users, or in yet another alternate embodiment the samples are generated or received at a slower rate where a facility may need to only provide samples at a lower rate.

Each given session within the system is registered to an RFID card, or other similar ID login, as described earlier. This ID login or RFID card contains a unique identification number, which is recorded within the database. Each card within the system is then linked to a member, who is then linked to a login account. These accounts are used to access the ECOFIT website 507 by a user in order to view personalized or group session data.

Each piece of equipment 501 within the system is considered a unique instance of a model of equipment, which contains any information that is not unique to a specific instance of equipment. Each piece of equipment also tracks its own location, as well as other important information such as serial number. These equipment model or location information is the basis for the definable data that is used by the system.

The database system 504 also makes use of promotions, which are limited offerings which allow additional ECOFIT Points to be earned. These promotions require an individual to meet certain requirements, including being in a specific location, during a specific time, and exceeding certain values in a given metric.

ECOFIT Points are tracked in independent "pools" of points, which are each stored separately to allow points to be redeemed to different purposes. This would allow a user to earn points for multiple organizations, all tracked to one account.

The database system 504 allows cards or other unique ID's to be registered to sessions without first being assigned to a member. This feature allows an end user to submit sessions using a card that they have not yet had the chance to register using the web interface. For example a facility may offer a guest or temporary user to utilize the machines and ECOFIT System in advance of actual user registration.

In one embodiment the ECOFIT Points Program allows ECOFIT members to earn ECOFIT Points while exercising. Metrics are gathered from the equipment the user is using and are sent as a session to the Database. At this point, the metrics are converted to points using a pre-defined algorithm. These points are credited to the user in the Database and can be exchanged at participating businesses for goods and services.

The website 507 which is served by the ECOFIT Server and Database 504, is generally designated herein as a Website System, allows direct access to the data stored within the Server and Database 504, as well as the ability to modify and input certain key points of user data. The end user interacts with the database system in order to view session data stored within the database 505, to register new ID cards to their login and member information, and to view options to redeem their points.

The website system will allow users to view all sessions which were submitted with their ID, such as an RFID card, which are registered to their account. These sessions will display all metrics captured as well as representations of activity over time through the sample system, either via the ECOFIT website 507 or other display device 508.

In one embodiment a user may have multiple cards registered to them at one time, and can add new cards to their account by entering the number or ID on the face of the card into the card registration interface. In an alternate embodiment the user has a single card or ID which is associated with them. For example a user may have a smartphone that has a RFID embedded in it which can be linked with the user login. This would enable a user to use their personal phone as the device to not only start and stop a session while at the equipment, but also use it as a single login for equipment that may be spread across multiple locations, such as a home equipment system enabled with the ECOFIT system, and a professional exercise facility which also has an ECOFIT system.

The ECOFIT website interface 507 also allows the user to view their points. Point totals for various pools will be shown, and the user can see what products and coupons their points can be applied towards. In addition to point totals, the user can see a record of all point transactions, including how many points were earned from each session. Also, the user can view promotions which they could potentially earn, filtered by which facilities and equipment they use most frequently.

Advertisers, facility managers, and other staff will also have access to function-specific portals which provide interfaces useful to their area of responsibility. Advertisers will be able to view the impact of advertising campaigns, facility managers will be able to see use statistics for their facility, and administrative staff will be able to manage members and their login information in order to provide customer service. These interfaces may be accessed separately from the standard user interface, and will may their own security processes and login information.

Configuration Interface

Figure 9:
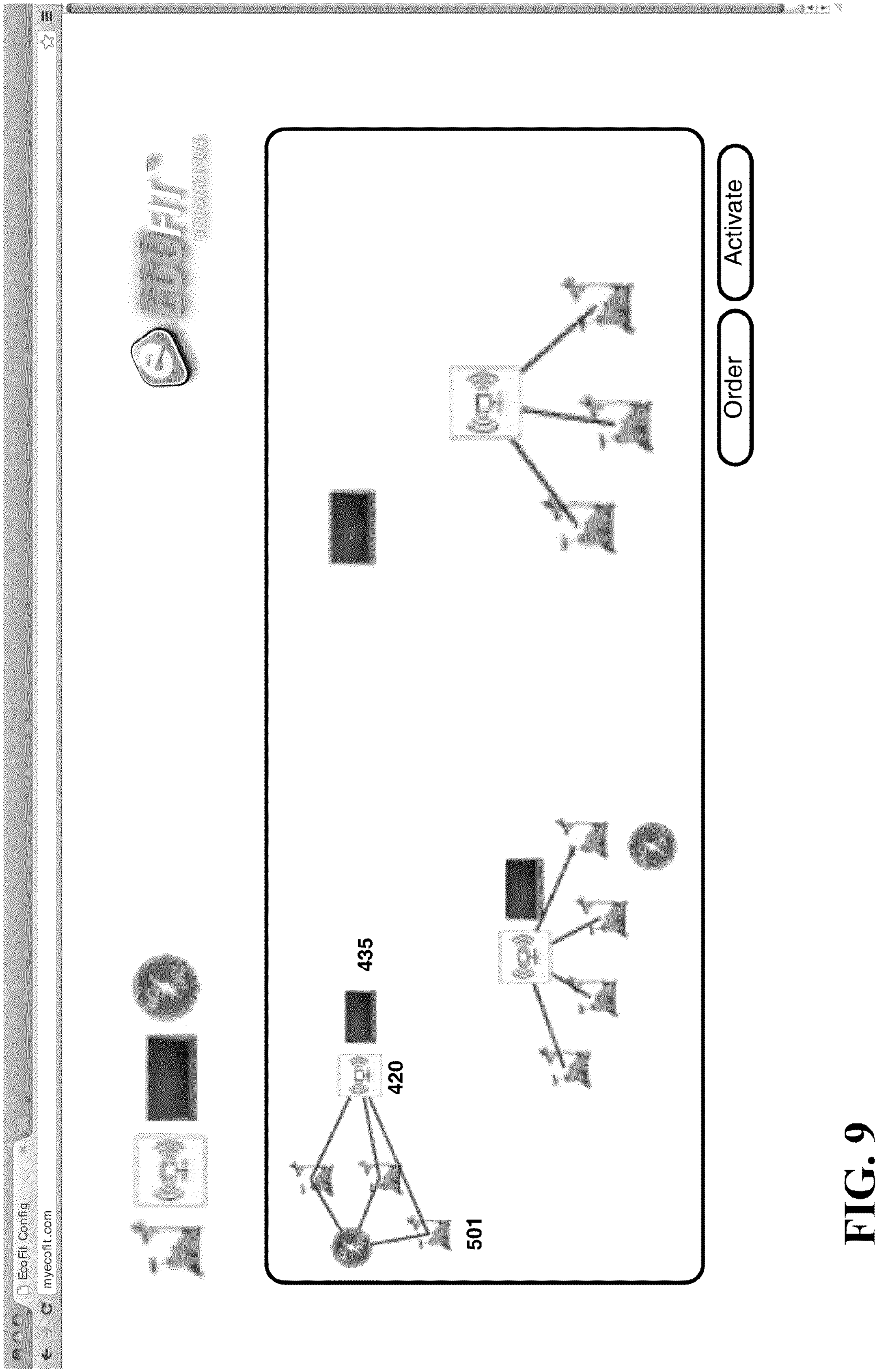
FIG. 9 illustrates an embodiment of an exemplary configuration web page.

An ECOFIT Local Installation 550 may be defined and altered by a facility through the ECOFIT Website 507 interface. Facility owners have the ability to log onto the ECOFIT Website 507 and build up an installation using a graphical interface wherein they can drag and drop basic ECOFIT installation elements. These elements include exercise equipment 501, Aggregators 420, Displays 435 and Inverters. Displays can be further customized for screen appearance, graphical software applications, such as Flash widgets may be used, and which equipment the consume data from. An example of an ECOFIT Web Configuration is shown in FIG. 9, where a user may configure to order or active a group of exercise equipment 501 with an associated Aggregator 420 and Display 435 for one location in the facility. It should be appreciated that the associated required equipment, such as the sensor nodes and base stations, are not illustrated in this visual representation, yet will be included in the local installation.

Once an installation has been created, an order summary may be sent to the ECOFIT device manufacturer and the order is prepared. The facility owner is billed and any required communication between the owner and ECOFIT is carried out. The equipment is prepared and installed at the facility. The final portion of the installation process is to activate the installation, again through the web interface 507. This will result the website 507, and the ECOFIT Server and Database 504 it is coupled with, to compile a series of configuration files outlining associations between the equipment at the facility. Configuration files are then transmitted the Displays 435 and Aggregators 420 after installation into the local facility 550. The Displays 435 use the configuration files to connect to the correct data feeds and to receive the correct content for the display software. The Aggregators 420 use the configuration files to associate to particular pieces of exercise equipment 501 through the Base Station 415 and the Wireless Links 410 or networks 520 to other data consuming devices as well as to translate raw metrics into ECOFIT metrics.

Targeted Advertisement and Demographic Metrics

The ECOFIT Server and Database 504 will also allow for targeted advertisement to users through ECOFIT Displays within facilities. When a user activates the system, the database 504 will be able to provide targeted content based on the users point redemption, equipment preferences, and demographic (age, sex, etc.).

In addition to providing targeted advertisements, the system can also be used to provide statistical information to advertising firms. This information may be any combination of data points from within the database system aggregated into an easy to understand form.

Maintenance Program

The Maintenance Program makes use of captured metrics to provide updates on the status of pieces of equipment 501 connected into the Server and Database 504 as well as tracking usage metrics for the purposes of scheduled maintenance. This system captures metrics from each individual piece of equipment and stores it in a central relational database system, which may reside on the ECOFIT Database and Server 504 or on a separate database such as the equipment manufacturer or the facility. This database tracks metrics relevant to each specific piece of equipment and stores them to enable reporting on a defined schedule. These reports are used to signal maintenance personnel when certain triggers are reached. Triggers are defined as sets of circumstances that require notification, and store within them the criteria under which a trigger would execute.

In addition to storing the ongoing use data of a piece of equipment for preventative maintenance, the system allows for the distribution of high priority error alerts. These are unexpected errors that come as the result of a catastrophic failure of the equipment. When such an error occurs at the equipment level, it is immediately stored in the database as its own report. This error is then immediately forwarded to the proper individual who can resolve the issue.

In the one example, a SportsArt use case, monitored exercise equipment is placed within gyms and exercise facilities. Members of the facilities (users) register accounts with the central database system using the web interface, and then use these cards when advertising. Session information is then used to credit individuals with points which can be redeemed for discounts at local business. The web site can then be used to view session information and track points. The maintenance system can then be used to track required maintenance statistics on the exercise equipment and dispatch maintenance staff as needed.

In another example, a SciFit use case, monitored exercise equipment is used within rehabilitation therapy clinics, physiotherapy clinics, and other medical facilities. Patients are given cards registered to their medical profiles. The equipment registers data with the central database system in order to track patient progress and to verify the outcome of courses of treatment. Customized web interfaces can be used by both patients and caretakers to track progress and analyze results. Aggregated information can be used to re-evaluate types of treatment and the results they produce. The maintenance system can then be used to track required maintenance statistics on the exercise equipment and dispatch maintenance staff as needed.

In another example monitored exercise equipment is placed within facilities in schools and tracks student data through the use of RFID cards assigned to individual students. This data is used to verify student progress in physical education classes. In addition to tracking progress, this data can be used to create lesson plans and grade students at the end of a course. Rich media displays in classes can be used to encourage students in their exercise and to pass on educational messages. The database system can be tied into educational social media games in order to encourage students to learn more about healthy life habits and choices. The maintenance system can then be used to track required maintenance statistics on the exercise equipment and dispatch maintenance staff as needed.

In another example a use case for the ECOFIT System is described, illustrating the use of captured metrics by various parties. Jane is an ECOFIT member and participates in spin classes at her local fitness club called Club Fitness. Every Sunday morning she goes to Club Fitness, gets on an available cycle equipment 501 and casually drops her ECOFIT card in the supplied trough on the cycle's display console. The RFID card is read by the embedded RFID reader in the trough, which is acts as the interface to the base station 415, and her name and current total ECOFIT Points are retrieved from the ECOFIT Database 505. On the ECOFIT Display 435 which faces the spin class, Jane's name appears along with her total points and bar graphs for her watts generated and her cumulative watt-hours total. To the right of the bar graphs, there are some local business advertisements running in a loop. The class begins, and Jane's watts bar graph begins to climb.

As Jane rides, the watts metric is captured from her spin cycle by the internal ECOFIT Sensor Node 405. The cycle that Jane is using is a SportsArt G572U, manufactured by SportsArt Fitness located in Taiwan, Republic of China., upright cycle which captures energy and feeds it back into the electrical grid. As Jane rides, the amount of energy she feeds back into the grid is communicated from the cycle's console over the CSAFE protocol to the Sensor Node 405 in the form of watts. The Sensor Node 405 then uses the ECOFIT Wireless Link 410 to transfer this raw watts metric to the ECOFIT Aggregator 420, which runs on the small form factor PC mounted behind the display at the front of the class. This raw metric is translated at the Aggregator 420 to the ECOFIT watts metric. From this point, the ECOFIT watts metric is cached as part of a record of Jane's current workout (session) and is also pushed out on the local network 520. The display 435 at the front of the class is attached to the same local network 520 and is configured to consume from the metric stream that the Aggregator 420 has made available. Jane's watt output metric is being displayed in real-time as a bar chart showing her progress. Jane's efforts are also being displayed at the Club Fitness front desk as part of a total class output. This front desk ECOFIT Display 511 shows spin class schedules and Club Fitness promotions as well.

The class has wrapped up, and Jane was happy to see from the display that she out-performed her rival on the cycle next to hers. These two ECOFIT users attend the same spin class every week and use competition as a way to motivate themselves. Jane triumphantly removes her ECOFIT card from the trough and invites her spin class competitor to spend the afternoon shopping.

Upon removing her card, Jane has completed her session from the point of view of the ECOFIT system. A session completion notification is passed up the Wireless Link 410 to the Aggregator 420 to indicate that there will be no more watts metrics. The session is closed at the Aggregator 420 and this is further communicated to the local network 520. The display at the front of the class shows an animation congratulating Jane for achieving top ECOFIT Points Leader status for this class. The display at the front desk indicates the good news as well.

The Aggregator 420 also uses this end-of-session indication to stop caching watts metrics and closes the session record. It then communicates this record to the ECOFIT Database 505 where it is stored. Jane's ECOFIT Points earned for the session are calculated and added to her current total. Jane has been engaged enough to fill out her ECOFIT profile with her email address and some simple information about herself. The Database uses this information to send Jane a quick email congratulating her on accumulating extra points and even breaking her own personal session record at Club Fitness. Jane's doing well today!

To celebrate their achievements, Jane and her competitive friend decide to treat themselves to a wholesome lunch at Good Foods local whole foods eatery, having seen their advertisement while working out. Good Foods is a participating business in the ECOFIT Points program and Jane uses her points to pay for her lunch this time.

Good Foods is interested in the effectiveness of their advertising. Once a month they receive a report compiled from the ECOFIT database and system 504 indicating how many times their ads have played, when they play, and statistics on who likely viewed the ads. They also see who of the ECOFIT members visit their eatery to use their points and which ads they likely viewed. Good Foods uses this information to better target their advertisements as well as to better understand and serve their guests. Jane and her friend finish their lunch and continue shopping.

In another example a use case for the ECOFIT System is described, illustrating the use of comparing users across multiple locations. Sherlock High school in Kansas City, Mo. wishes to improve their Physical Education program. Currently they don't feel that they can assess student progress effectively as well as keep students interested and engaged in PE classes.

To improve the situation, Sherlock High school has recently invested in fitness equipment enhanced with the ECOFIT System. They have mounted an ECOFIT Display 435 in the gym and have a class total output visible on-screen. The equipment 501 they chose is varied and includes cycles, treadmills and ellipticals and each one has an integrated heart rate monitor. They have chosen to use heart rate as a metric to grade individual students on. The equipment manufacturer and the school have a mutual desire to stay informed of how much the equipment is being used and when they might need maintenance.

Interestingly enough, Moriarty Secondary (Sherlock's greatest rival) has also bought into the ECOFIT System in the hopes of alleviating similar issues with its PE program. These two schools often grapple for placement in Football and Basketball city-wide.

After a few weeks and many PE classes, Sherlock has noted improved efficiency and accuracy in grading thanks to the system. Individual student performance is easily tracked using ECOFIT cards (each one associated to a student as well as their personal information such as height, weight, age etc.). The ECOFIT web portal can be easily queried for student performance and achievements. Students as well have become far more engaged, the display has a "cool factor" and they enjoy accessing their performance information through the ECOFIT website student portal as well as having their fitness achievements posted to their Facebook accounts if they so choose. Even better, Sherlock High school has been regularly destroying Moriarty Secondary in inter-school competitions through the ECOFIT system during concurrent PE classes of similar age and ability.

The equipment manufacturer that had generously supplied the fitness equipment at cost has been regularly accessing the ECOFIT website manufacturer portal to get statistics on the usage of their machines. They use information such as what equipment is being used for how long to better assess how they might supply equipment to other schools interested in the same program. They also use failure notifications through the ECOFIT Maintenance Program to better understand what fails on their equipment and improve their designs.

Both Sherlock High school and Moriarty Secondary also enjoy the benefits of the Maintenance Program which allows them to have their equipment up and running for more time and to prevent catastrophic failures through improved maintenance scheduling.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

It is therefore intended that the foregoing detailed description be regarded as illustrative rather than limiting, and that it be understood that it is the following claims, including all equivalents, that are intended to define the spirit and scope of this invention.

What is claimed is:

1. A system for monitoring usage of a plurality of pieces of exercise equipment, the system comprising:

a base station operative to wirelessly communicate with each piece of exercise equipment of the plurality of pieces of exercise equipment and to receive usage metric data, indicative of the current utilization of each piece of exercise equipment, while the piece of exercise equipment is being utilized, wherein the base station further includes:

a first radio over which the base station transmits a data request for usage metric data to each piece of exercise equipment of the plurality of pieces of exercise equipment and listens for a response therefrom, each data request identifying the piece of exercise equipment and specifying a set of channels for the identified piece of exercise equipment to utilize for transmitting its response to the base station, the base station being operative to listen for the response on each of the specified channels in turn for a defined period of time until the response has been received or all of the specified channels have been listened to; and a second radio over which the base station is further operative to transmit, over each of a plurality of channels in turn, a sync request to any piece of exercise equipment from which a response was not received over any of the specified channels, the sync request comprising an identifier of the non-responsive piece of exercise equipment and a channel of the first radio on which the non-responsive piece of exercise equipment should listen for a data request from the base station; and wherein the system further includes:

an aggregator coupled with the base station and operative to aggregate the received usage metric data for each piece of exercise equipment as it is received by the base station, addressably combine the aggregated received usage metric data for each piece of exercise equipment and broadcast the addressably combined aggregated received usage metric data over a network, wherein one or more devices coupled thereto may access aggregated received usage metric data of one or more particular pieces of exercise equipment of the plurality of pieces of exercise equipment from the broadcasted addressably combined usage metric data.

2. The system of claim 1 wherein the base station receives no usage metric data from a piece of exercise equipment that is not being currently utilized.

3. The system of claim 1 wherein the base station is operative to request usage metric data from each piece of exercise equipment, the received usage metric data being responsive to the request.

4. The system of claim 1 wherein the received response from a piece of exercise equipment includes a request by the piece of exercise equipment to send additional data, the base station being operative, responsive thereto, to transmit another data request to the piece of exercise equipment.

5. The system of claim 1 wherein the base station communicates with each piece of exercise equipment using a first protocol, and the addressably combined aggregated received usage metric data is broadcasted in a second protocol different from the first protocol.

6. The system of claim 1 wherein the received usage metric data is periodically received.

7. The system of claim 1 wherein the addressably combined aggregated received usage metric data comprises a User Datagram Protocol ("UDP") multicast format.

8. The system of claim 1 wherein the one or more devices ignore aggregated received usage metric data of the remaining pieces of exercise equipment of the plurality of pieces of exercise equipment.

9. The system of claim 1 wherein each piece of exercise equipment is assigned a unique identifier, the unique identifier used to address the aggregated received usage metric data received therefrom in the addressably combined aggregated received usage metric data wherein any of the one or more devices may access the aggregated received usage metric data of a particular piece of exercise equipment from the broadcasted addressably combined aggregated received usage metric data based on the unique identifier assigned to the particular piece of exercise equipment.

10. The system of claim 9 wherein the unique identifier comprises a User Datagram Protocol ("UDP") port number.

11. The system of claim 1 wherein any of the one or more devices coupled with the network may substantially simultaneously access the broadcasted addressably combined usage metric data.

12. The system of claim 1 wherein the base station and aggregator are separate devices.

13. The system of claim 1 wherein the network comprises a dedicated sub-network which only carries the broadcasted addressably combined aggregated received usage metric data.

14. The system of claim 1 wherein the base station is further operative to receive the usage metric data from a sensor coupled with the exercise machine, the sensor being operative to extract the usage metric data therefrom.

15. A computer implemented method for monitoring usage of a plurality of pieces of exercise equipment, the method comprising:

receiving, by a processor wirelessly, usage metric data, indicative of the current utilization of each piece of exercise equipment, while the piece of exercise equipment is being utilized, the receiving further comprising:

transmitting, via a first radio, a data request for usage metric data to each piece of exercise equipment of the plurality of pieces of exercise equipment and listening for a response therefrom, each data request identifying the piece of exercise equipment and specifying a set of channels for the identified piece of exercise equipment to utilize for transmitting its response to the base station, the listening further comprising listening for the response on each of the specified channels in turn for a defined period of time until the response has been received or all of the specified channels have been listened to; and transmitting, via a second radio over each of a plurality of channels in turn, a sync request to any piece of exercise equipment from which a response was not received over any of the specified channels, the sync request comprising an identifier of the non-responsive piece of exercise equipment and a channel of the first radio on which the non-responsive piece of exercise equipment should listen for a data request from the base station; and wherein the method further includes:

aggregating, by the processor, the received usage metric data for each piece of exercise equipment as it is received;

addressably combining, by the processor, the aggregated received usage metric data for each piece of exercise equipment; and broadcasting, by the processor, the addressably combined aggregated received usage metric data over a network; and wherein one or more devices coupled thereto may access aggregated received usage metric data of one or more particular pieces of exercise equipment of the plurality of pieces of exercise equipment from the broadcasted addressably combined usage metric data.

16. The method of claim 15 wherein usage metric data is not received from a piece of exercise equipment that is not being currently utilized.

17. The method of claim 15 further comprising requesting, by the processor, usage metric data from each piece of exercise equipment, the received usage metric data being responsive to the request.

18. The method of claim 15 wherein the received response a piece of exercise equipment includes a request by the piece of exercise equipment to send additional data, the method further comprising transmitting another data request to the piece of exercise equipment.

19. The system of claim 1 wherein the usage metric data is received using a first protocol, and the addressably combined aggregated received usage metric data is broadcasted in a second protocol different from the first protocol.

20. The method of claim 15 wherein the received usage metric data is periodically received.

21. The method of claim 15 wherein the addressably combined aggregated received usage metric data comprises a User Datagram Protocol ("UDP") multicast format.

22. The method of claim 15 wherein the one or more devices ignore aggregated received usage metric data of the remaining pieces of exercise equipment of the plurality of pieces of exercise equipment

23. The method of claim 15 wherein each piece of exercise equipment is assigned a unique identifier, the unique identifier used to address the aggregated received usage metric data received therefrom in the addressably combined aggregated received usage metric data wherein any of the one or more devices may access the aggregated received usage metric data of a particular piece of exercise equipment from the broadcasted addressably combined aggregated received usage metric data based on the unique identifier assigned to the particular piece of exercise equipment.

24. The method of claim 23 wherein the unique identifier comprises a User Datagram Protocol ("UDP") port number.

25. The method of claim 15 wherein any of the one or more devices coupled with the network may substantially simultaneously access the broadcasted addressably combined aggregated received usage metric data.

26. The method of claim 15 wherein the base station and aggregator are separate devices.

27. The method of claim 15 wherein the network comprises a dedicated sub-network which only carries the broadcasted addressably combined aggregated received usage metric data.

28. The method of claim 15 wherein the usage metric data is received from a sensor coupled with the exercise machine, the sensor being operative to extract the usage metric data therefrom.

29. A system for monitoring usage of a plurality of pieces of exercise equipment, the system comprising:

first logic stored in a memory and executable by a processor coupled therewith to cause the processor to receive usage metric data, indicative of the current utilization of each piece of exercise equipment, while the piece of exercise equipment is being utilized;

the first logic being operative to cause the processor to transmit, via a first radio, a data request for usage metric data to each piece of exercise equipment of the plurality of pieces of exercise equipment and listen for a response therefrom, each data request identifying the piece of exercise equipment and specifying a set of channels for the identified piece of exercise equipment to utilize for transmitting its response to the base station, the first logic being operative to cause the processor to listen for the response on each of the specified channels in turn for a defined period of time until the response has been received or all of the specified channels have been listened to; and the first logic being operative to cause the processor to transmit, via a second radio over each of a plurality of channels in turn, a sync request to any piece of exercise equipment from which a response was not received over any of the specified channels, the sync request comprising an identifier of the non-responsive piece of exercise equipment and a channel of the first radio on which the non-responsive piece of exercise equipment should listen for a data request from the base station; and wherein the system further includes:

second logic stored in the memory and executable by the processor to cause the processor to aggregate the received usage metric data for each piece of exercise equipment as it is received by the base station, addressably combine the aggregated received usage metric data for each piece of exercise equipment and broadcast the addressably combined aggregated received usage metric data over a network, wherein one or more devices coupled thereto may access aggregated received usage metric data of one or more particular pieces of exercise equipment of the plurality of pieces of exercise equipment from the broadcasted addressably combined usage metric data.

* * * * *